(12) United States Patent
Shin et al.

(10) Patent No.: US 8,911,462 B2
(45) Date of Patent: Dec. 16, 2014

(54) ONE BODY LANCET AND NO PAIN TYPE BLOOD COLLECTING DEVICE

(75) Inventors: Youn-Choul Shin, Gangneung-si (KR); Suk-Jin Jang, Donghae-si (KR)

(73) Assignee: Bosung Meditech Co., Ltd., Wonju-Si (KR)

( * ) Notice: Subject to any disclaimer, the term of this patent is extended or adjusted under 35 U.S.C. 154(b) by 637 days.

(21) Appl. No.: 13/001,844

(22) PCT Filed: Sep. 30, 2008

(86) PCT No.: PCT/KR2008/005743
§ 371 (c)(1),
(2), (4) Date: Dec. 29, 2010

(87) PCT Pub. No.: WO2010/002072
PCT Pub. Date: Jan. 7, 2010

(65) Prior Publication Data
US 2011/0106127 A1 May 5, 2011

(30) Foreign Application Priority Data
Jul. 3, 2008 (KR) ........................ 10-2008-0064605

(51) Int. Cl.
*A61B 17/14* (2006.01)
*A61B 5/15* (2006.01)

(52) U.S. Cl.
CPC .................................... *A61B 5/1411* (2013.01)
USPC ....................................................... 606/182

(58) Field of Classification Search
USPC ................... 606/181, 182, 184, 204
See application file for complete search history.

(56) References Cited

U.S. PATENT DOCUMENTS

| 4,517,978 | A | | 5/1985 | Levin et al. |
| 5,211,652 | A | * | 5/1993 | Derbyshire .................. 606/182 |
| 5,749,886 | A | * | 5/1998 | Abidin et al. ................. 606/182 |
| 5,755,733 | A | * | 5/1998 | Morita .......................... 606/182 |
| 6,730,046 | B1 | | 5/2004 | Hamamoto et al. |

(Continued)

FOREIGN PATENT DOCUMENTS

| JP | 678903 A | 3/1994 |
| JP | 2003339680 A | 12/2003 |
| JP | 2006305143 A | 11/2006 |
| JP | 200754379 A | 3/2007 |

*Primary Examiner* — Kathleen Holwerda
*Assistant Examiner* — Sarah Simpson
(74) *Attorney, Agent, or Firm* — The Webb Law Firm (57) ABSTRACT

The present invention concerns a blood withdrawal device comprising a one-piece cap and lancet and a painless impulse generator. The object of the present invention is to withdraw blood painlessly and to reduce a risk of a secondary infection. In order to achieve the object of the present invention, the blood withdrawal device of the present invention comprises a cap, a hollow body and a painless blood withdrawal device. The cap comprises a one-piece cap and lancet within which a lancet is movably combined and a hollow body for a detachable connection with a painless impulse generator or a main body of a blood withdrawal device. The hollow body comprises open ends on both side of the body thereby allowing the lancet to be detachable and the movable axis to be inserted within the body. The painless impulse generator is connected with the main body of the blood withdrawal device through a means for connecting with the main body of the blood withdrawal device defined at one side of the body thereby allowing the movement of the lancet needle and the cap by the movable axis. Therefore painless blood withdrawal is possible.

6 Claims, 9 Drawing Sheets

(56) References Cited

U.S. PATENT DOCUMENTS

| | | | |
|---|---|---|---|
| 6,866,675 B2 * | 3/2005 | Perez et al. | 606/181 |
| 8,021,382 B2 * | 9/2011 | Shi | 606/182 |
| 2005/0209625 A1 * | 9/2005 | Chan | 606/181 |
| 2007/0055298 A1 * | 3/2007 | Uehata et al. | 606/181 |
| 2007/0244498 A1 * | 10/2007 | Steg | 606/181 |

* cited by examiner

ONE BODY LANCET AND NO PAIN TYPE BLOOD COLLECTING DEVICE

TECHNICAL FIELD

The present invention concerns a cap of a one body lancet (hereinafter called "a one-piece cap and lancet"), a blood withdrawal device and an acupuncture treatment device with a painless impulse generator. In particular, the aforementioned cap combined with a lancet, thus forming one body, may be integrated or disintegrated to a painless impulse generator or a blood withdrawal device. This invention particularly relates to a no pain type blood withdrawal device (hereinafter called "a painless blood withdrawal device") and an acupuncture treatment device that remarkably reduces pain by exerting an impulse on an adjacent body part at the time of a puncturing.

BACKGROUND ART

In general, blood withdrawal devices are used to draw blood samples for analytical purposes and particularly are used by diabetics who must regularly monitor their blood glucose levels. Lancet devices are commonly used to prick the skin so that a few drops of blood may be extracted for testing. The lancet, which typically has a needle fixed to a holder, forces the needle out of the device so that the needle can penetrate the skin.

An example is described in U.S. Pat. No. 4,517,978 in which a lancet has a needle that is attached to and is engaged with a main body. By pressing the trigger of the invention of the abovementioned patent document, the sleeve of the main body is pulled and then the lancet moves forward so that the needle can penetrate the skin for withdrawal of blood. Immediately thereafter the lancet is retracted.

In general, a needle held in a lancet is moved at a high speed in order to withdraw blood by producing a wound in a body part that causes a pain associated with the production of the puncture wounds necessary for the withdrawal of blood, which is problematic. Hence it is desirable to develop a painless blood withdrawal device, especially for those who draw blood samples for analytical purposes and for diabetics who frequently withdraw blood by themselves.

In cases where several patients are tested consecutively such as in hospitals, there is often a risk of a spread of infection by the use of a single lancet device on more than one patient. In order to counteract such problems, the use of a disposable lancet became mandatory. Therefore disposable lancets should be used in hospitals where several patients are tested consecutively. Hence it is also desirable to develop a painless blood withdrawal device with a disposable lancet.

Already several attempts have been made in the prior art to reduce pain associated with the lancing by reducing the thickness of the tip of the needles. However there is a technical limitation for reducing the thickness of the tip of the needles since the needle protective cap is designed to be removed from the main body by human hand.

DISCLOSURE OF INVENTION

Technical Problem

The object of the present invention is to propose a one-piece cap and lancet that is designed for a lancet to be fixed to the internal space of a cap of a hollow body so that the lancet moves along a predetermined lancing path. The lancet together with a cap is detachably combined with a painless impulse generator or a main body of the blood withdrawal device.

Another object of the present invention is to propose a painless blood withdrawal device and an acupuncture treatment device that remarkably reduces pain by exerting an impulse using a painless impulse generator on an adjacent body part at the time of a puncturing.

Another object of the present invention is to propose a painless blood withdrawal device that is detachably combined with a one-piece cap and lancet. By using the one-piece cap and lancet, the danger of a secondary infection can be remarkably reduced and by using the painless impulse generator, blood withdrawal can be achieved without pain.

Technical Solution

In one embodiment, the present invention provides a one-piece cap and lancet that is detachably combined with a painless impulse generator or a main body of the blood withdrawal device by simply providing an internal space within a hollow body of a cap for inserting the lancet and an elastic element inside the internal space so that the lancet can move along a predetermined lancing path.

The present invention of the embodiment provides a one-piece cap and lancet comprising a hollow body cap, a lancet body and an elastic element. The hollow body cap comprises an multi step structured internal space within which a lancet is movable, a shoulder for an elastic element to stop the forward movement of the lancet, an opening for a needle defined at the front end of the hollow body cap and a projection for a lancet defined at the rear end of the inner circle of the hollow body cap. The lancet body is movably contained within the internal space of the hollow body cap, wherein a needle is fixed at the front end of the lancet body and a lancet holding member is defined at the rear end of the lancet body to prevent an escape of the lancet. The needle moves along the predetermined path through the opening for allowing the needle to advance therethrough. The elastic element provides elasticity for the movement of the lancet together with a lancet body contained in an internal space of a hollow body cap.

The elastic element of the one-piece cap and lancet which provides elasticity for the movement of the lancet is defined between the shoulder for the elastic element and the lancet holding member of the lancet body.

The said elastic element of the one-piece cap and lancet can be a spring which extends between the lancet holding member and said shoulder for the elastic element. The spring forms a zigzag pattern perpendicular to the lancing direction. The elastic element comprises a pair and the pair is symmetrical to said lancet.

The said elastic element of the one-piece cap and lancet can be detachable from the lancet and forms a shape of a jar whose middle is convex to bend toward the lancet body, wherein one end of the elastic element is connected to the shoulder for the elastic element and the other end is connected to the lancet holding member. Another example of the elastic element is detachable from the lancet and forms a shape of an hourglass drum whose middle is concave to bend inner side of the lancet body, wherein one end is connected to the shoulder for the elastic element and the other end is connected to the lancet holding member. The elastic element can be comprised of two or more rings overlapped to strengthen elasticity.

The said elastic element of the one-piece cap and lancet can be a coil spring. In this case, the said cap comprises an internal space for said lancet in which the lancet moves along the predetermined path, an internal space for said elastic element in which the elastic element moves along the predetermined path and an internal space for said lancet holding member in which the lancet holding member moves along the predetermined path. The above mentioned three internal spaces are connected by multi step with the fine radius differences wherein the shoulder for said elastic element and the end for said lancet holding member may prevent the forward movement of the elastic element and the lancet holding member as the lancet moves forward.

Also the one-piece cap and lancet of the present invention can be designed with a needle protective cap at the front end of said lancet body. The needle protective cap can be designed multangular and the shape of the opening for the needle is also multangular corresponding to that of said cap. Furthermore the one-piece cap and lancet comprises a rotate stop pin which is arranged at the rear end of the lancet holding member to prevent a rotation of the lancet body. An insert hole for said rotate stop pin is arranged at the front end of a depth adjusting element. And said depth adjusting element is assembled to a painless impulse generator or a main body of a blood withdrawal device.

According to another example of present invention to achieve the aforementioned object, the painless blood withdrawal device comprises a movable axis which moves the lancet in lancing direction, a cap defined at the front end of a main body and a painless impulse generator comprising a hollow body with connection units for a cap and a main body of a blood withdrawal device at the front and rear ends respectively. The painless impulse generator comprises a gearing element which is defined within said hollow body of the painless impulse generator. The gearing element moves along with said movable axis in said lancing direction thereby moving said cap.

According to another example of present invention to achieve the aforementioned object, the painless blood withdrawal device comprises a movable axis which moves the lancet in lancing direction, a cap being defined at the front end of main body, a painless impulse generator comprising a hollow body with connection units for a cap and a main body of a blood withdrawal device at front and rear ends respectively. The painless impulse generator comprises a gearing element which is defined within said hollow body of the painless impulse generator. The gearing element moves along with said movable axis in said lancing direction thereby moving said cap. Also the painless blood withdrawal device further comprises a movable axis retraction unit which is inserted within the movable axis and is defined between the painless impulse generator and the main body of a blood withdrawal device thereby pushing forward said painless impulse generator when said movable axis moves forward and retracting said movable axis, a lancet holder which is defined at the front end of said movable axis, a lancet which is fixed at the lancet holder and a cap comprising a hollow body. Wherein said lancet and lancet holder which is inserted within said hollow body of the cap thereby allowing backward and forward movement of said cap is detachable from said painless impulse generator.

According to another example of present invention to achieve the aforementioned object, the painless blood withdrawal device comprises a movable axis which moves the lancet in lancing direction, a cap being defined at the front end of main body, a painless impulse generator comprising a hollow body with connection units for a cap and a main body of a blood withdrawal device at front and rear ends respectively. The painless impulse generator comprises a gearing element which is defined within said hollow body of the painless impulse generator. The gearing element moves along with said movable axis in said lancing direction thereby moving said cap. Also the painless blood withdrawal device further comprises a movable axis retraction unit which is inserted within a movable axis and is defined between a painless impulse generator and a main body of a blood withdrawal device thereby pushing forward said painless impulse generator when said movable axis moves forward and retracting said movable axis and a one-piece cap and lancet. Wherein said cap comprises a hollow body within which the lancet moves along a predetermined lancing path. The one-piece cap and lancet is detachably combined with a painless impulse generator or a main body of the blood withdrawal device through said hollow body of said cap.

Each of above examples of the painless blood withdrawal device further comprises a depth adjusting element of which one end is combined with said painless impulse generator and the other end is combined with the replaceable cap. The said depth adjusting element is designed to rotate through the outer circle while combined with the painless impulse generator. Also the said depth adjusting element changes the distance between the cap and the main body of the blood withdrawal device by changing a degree of rotation thereby controlling the depth of the penetration of the needle.

Each of above examples of the painless blood withdrawal device further comprises a power supply supplying a pulse power through an instantaneous pulse wave circuit thereby allowing a forward movement of a movable axis and an impulse generator switch controlling a pulse power of said power supply resulting in a strike type painless blood withdrawal device.

For each of above examples of the painless blood withdrawal device, a one-piece cap and lancet or a cap with a replaceable lancet can be made of a conductible touch panel and further comprises a touch circuit driven by said touch panel and a power supply for applying a pulse power through an instantaneous pulse wave circuit thereby forming a touch type painless blood withdrawal device.

For each of above examples of the painless blood withdrawal device of the present invention, a voltage applied to a movable axis is controlled by a value set by an impulse strength adjusting element thereby controlling impulse strength of a skin.

The painless impulse generator of each of above examples of the painless blood withdrawal device may comprise a partition with a hole which is defined within said hollow body in order to restrict the movement of said movable axis or a retraction unit of said movable axis.

The painless impulse generator of each of the above examples of the painless blood withdrawal device of the present invention comprises a fixed sleeve, a gearing sleeve and a buffering unit. The said fixed sleeve comprises a hollow body of which diameter is suitable for a connection with the outlet of the main body of the blood withdrawal device. Both ends of said fixed sleeve are open so that an end for a gearing sleeve is defined inside of one end and a connection unit with a main body is defined at the other end. The said gearing sleeve comprises a hollow body of which diameter is suitable for an insertion within said fixed sleeve and a partition with a hole for steering a movable axis is defined within said hollow body of said gearing sleeve. Furthermore an end for a fixed sleeve corresponding to an end for a gearing sleeve is defined on the outer circle of one end of said body and a lancet connection unit with a cap is defined at the other end. The said buffering unit, which is inserted within an inner circle of said gearing sleeve, is arranged between said gearing and fixed sleeves and can be compressed or retracted through said ends for the fixed and gearing sleeves.

Advantageous Effects

The painless blood withdrawal device of the present invention is advantageous for painlessly withdrawing blood through providing an impulse to an adjacent body part simultaneously with piercing a skin.

Also the painless blood withdrawal device of present invention is advantageous for providing an easily attachable/detachable lancet thereby remarkably reducing a risk of a secondary infection.

BEST MODE FOR CARRYING OUT THE INVENTION

Figure 2:
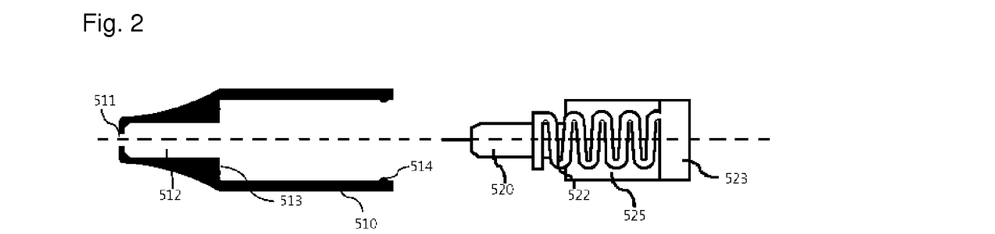
FIG. 2 is a partial cutaway diagram of FIG. 1.

The desirable example of the present invention is a one-piece cap and lancet (500a) constructed in accordance with a first example. As shown in FIG. 2, the one-piece cap and lancet (500a) comprises a hollow body cap (510) within which a lancet is contained, a lancet body (520) defined within the cap moving along the predetermined path and an elastic element (522) inserted within the internal space of said cap. The elastic element (522) is combined with the lancet body.

A detailed explanation on each element of said one-piece cap and lancet will be given in the following examples.

MODE FOR THE INVENTION

Example embodiments of the present invention are described herein with reference to the figures.

Figure 1:
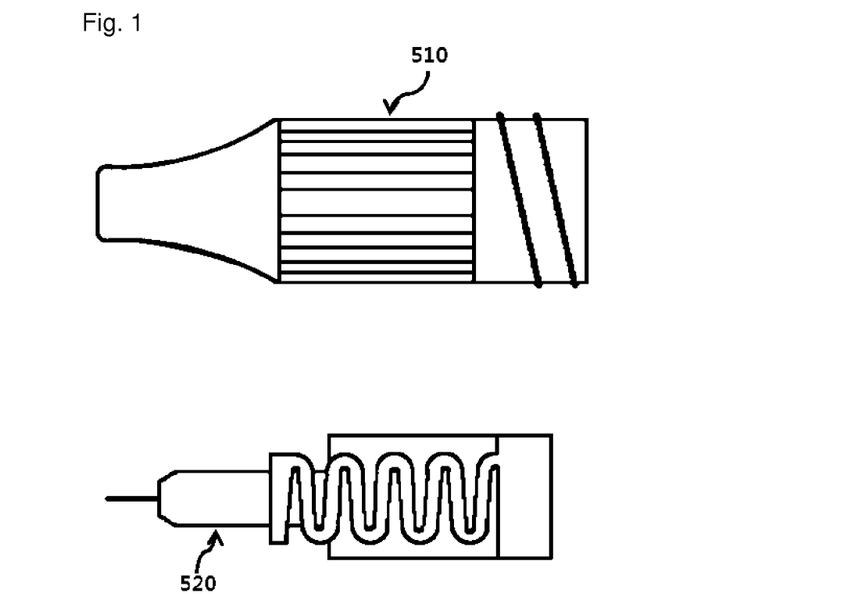
FIG. 1 is a side view of a one-piece cap and lancet of a first example of the present invention.
Figure 3:
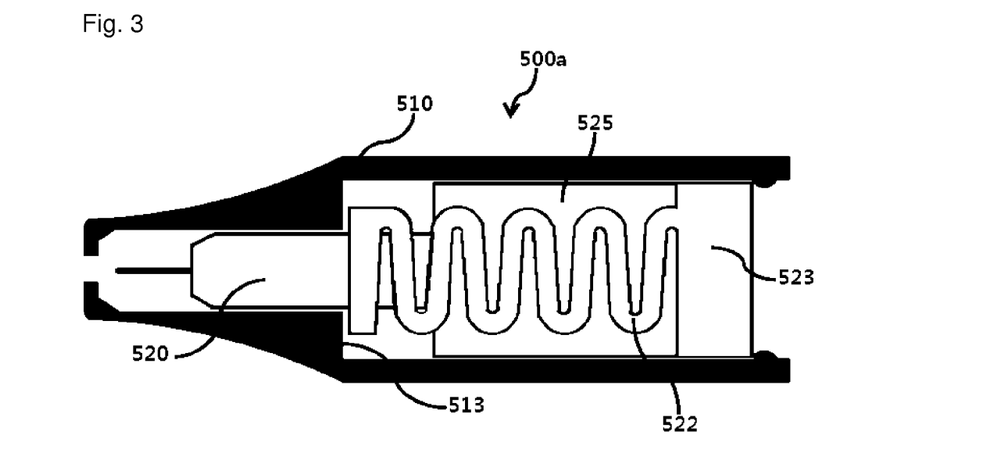
FIG. 3 and FIG. 4 are a side view and a plane view of FIG. 1.
Figure 4:
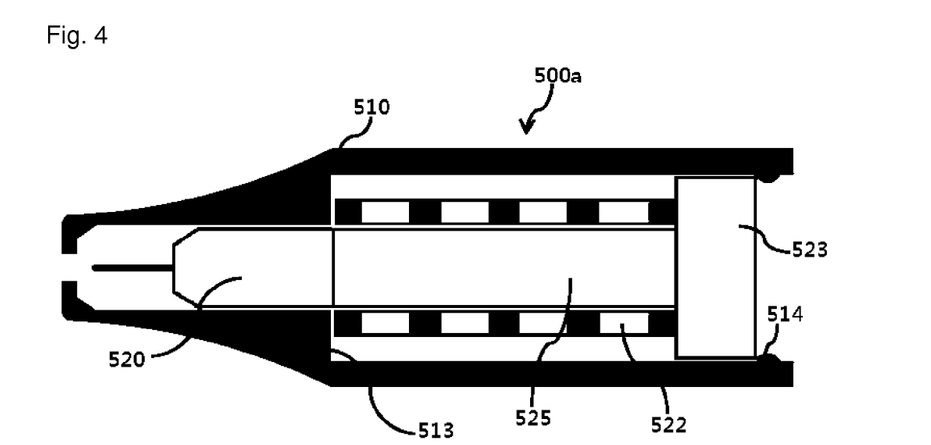

FIG. 1 is a side view of a one-piece cap and lancet of a first example of the present invention, FIG. 2 is a partial cutaway diagram of FIG. 1 and FIG. 3 and FIG. 4 are a side view and a plane view of FIG. 1 which present a one-piece cap and lancet (500a) of a first example of the present invention that can be inserted within a depth adjusting element.

As shown in FIG. 1-FIG. 4, the one-piece cap and lancet (500a) comprises a hollow body cap (510) within which an internal space for the lancet is defined, a lancet body (520) movable along a predetermined path within the cap and an elastic element (522) combined with said lancet body within said internal space for the lancet.

The cap (510) comprises an internal space for the lancet (512) within which said lancet is movable. The said internal space (512) forms a multi step structure which engages a shoulder for an elastic element (513) to stop the forward movement of the lancet. Also, an opening for a needle (511) is defined at the front end of the hollow body cap and a projection for a lancet (514) is defined at the rear end of the inner circle of the hollow body cap to prevent an escape of the lancet from the cap.

The lancet body (520) is movably contained within an internal space (512) of a hollow body cap. A needle is fixed at the front end of the lancet body and a lancet holding member (523) is formed at the rear end of the lancet body to prevent escape of the lancet. A lancet supporting member (525) is extended from the lancet holding member (523) to support the lancet body. The needle moves along the predetermined path through the opening (511) for allowing the needle to advance therethrough.

The elastic element (522) providing elasticity for the movement of the lancet is contained within the internal space together with the lancet body.

As shown in FIG. 1-FIG. 4, the elastic element (522) is formed on both sides of the lancet supporting member (525) and is a spring forming a zigzag pattern perpendicular to the lancing direction. The elastic element (522) extends from the lancet holding member (523) toward the front of the lancet body with an open end so that said open end is connected to the shoulder for the elastic element (513) of the cap (510). The elastic element (522) comprises a pair and the pair is symmetrical to the said lancet.

Figure 5:
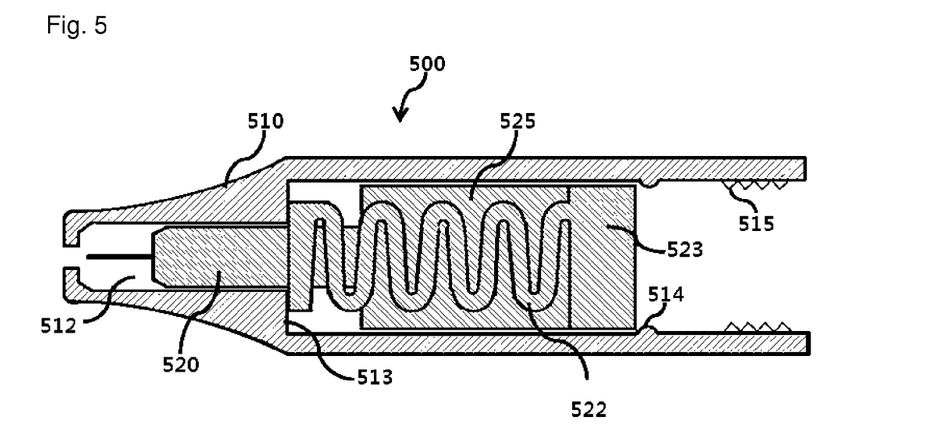
FIG. 5 is a sectional view of a main body which is arranged at an opening of a one-piece cap and lancet of a first example of the present invention.

FIG. 5 is a sectional view of a one-piece cap and lancet (500) as another example of one-piece cap and lancet (500a) of the first example of the present invention. The technical feature of the one-piece cap and lancet (500a) lies on an extended part at the rear open end of the one-piece cap and lancet (500a) thereby forming a means for connecting with a main body (515). Though FIG. 5 presents the means for connecting with a main body (515) formed in the inner side of the cap (510), it can be formed at the outer side of the cap.

Figure 6:
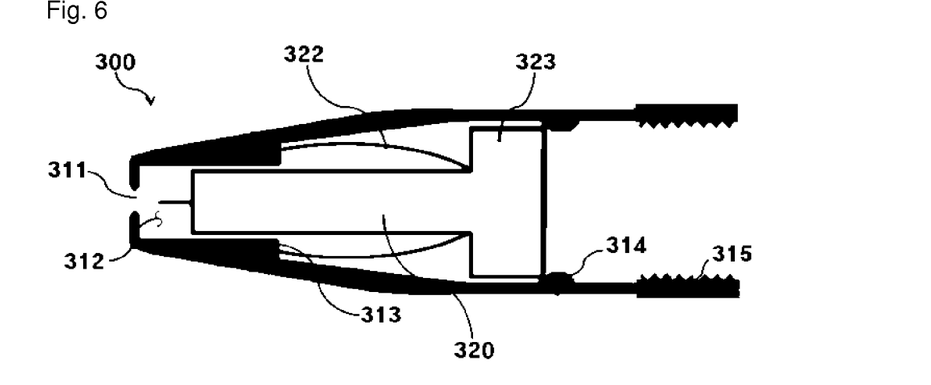
FIG. 6 is a sectional view of a one-piece cap and lancet of a second example of the present invention.

FIG. 6 is a sectional view of the one-piece cap (300) of the second example comprising an elastic element (322) of a shape of a jar whose middle is convex to bend toward the lancet body As shown in FIG. 6 the one-piece cap and lancet (300) of the second example comprises the cap (310), the lancet body (320) and the elastic element (322).

The cap (310) is defined with an opening for a needle (311) allowing the needle to advance therethrough. As shown in the FIG. 6, an internal space (312) is formed at the front part of the cap so that the lancet is movable within the internal space. Also, a shoulder for the elastic element (313) is formed at the rear part of the internal space along the inner side of the body of the cap so that the elastic element of the lancet can be fixed. A projection for the lancet (314) is formed at the rear part of the cap projected from the inner side of the body of the cap so that the lancet can be fixed within the cap. Also at the rear part of the projection for the lancet, a means for connecting with the painless impulse generator (315) using a screw type connection is formed to connect with the outer side of the gearing sleeve (152: see FIG. 12) of the painless impulse generator (150).

The lancet body (320) comprises a lancet needle defined at the front part of the body and a lancet holding member (323) defined at the rear part of the body.

The elastic element (322) detachable from the lancet body comprises a shape of a jar whose middle is convex to bend toward the lancet body. One end of the elastic element is connected to the shoulder for the elastic element (313) and the other end is to the lancet holding member (323) and the elastic element is made of a silicone rubber and similar material. The elastic element detachable from the lancet body which is not shown in the figure can also comprise a shape of an hourglass drum whose middle is concave to bend inner side of the lancet body. In this case as well, one end of the elastic element is connected to the shoulder for the elastic element (313) and the other end is to the lancet holding member (323). Both jar and hourglass shape of the elastic element (322) can be comprised of two or more rings overlapped and the number of rings can be defined depending on the necessary elasticity thereby providing an appropriate elasticity for the movement of the lancet body.

Figure 7:
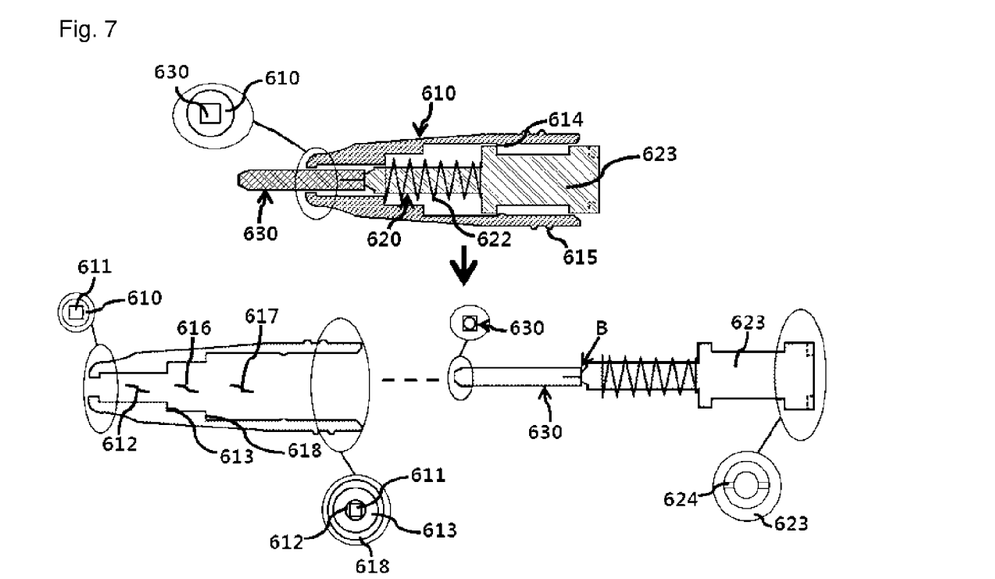
FIG. 7 is a sectional view of an assembled and disassembled one-piece cap and lancet (600) of a third example of the present invention.
Figure 8:
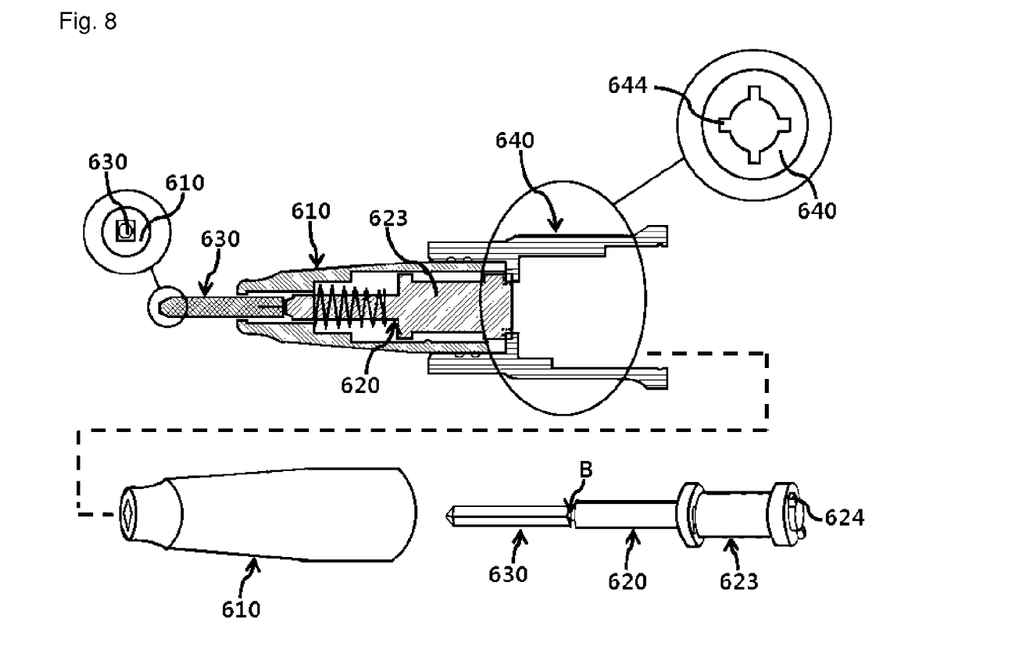
FIG. 8 is a sectional view and a partial cutaway diagram of a one-piece cap and lancet (600) of FIG. 7 combined with a depth adjusting element of a main body.

FIG. 7 is a sectional view of the assembled and disassembled one-piece cap and lancet (600) of the third example and FIG. 8 is a sectional view and a partial cutaway diagram of a one-piece cap and lancet (600) of FIG. 7 combined with a depth adjusting element of a main body. The one-piece cap and lancet (600) of the third example comprises a cap (610), a lancet body (620), an elastic element (622) and a needle protective cap (630).

As shown in FIG. 7 and FIG. 8, an opening for a needle (611) is defined at the front end of the cap (610) and a projection for a lancet (614) is defined at the rear end of the cap along the inner side of the cap. The shape of the said opening for a needle (611) corresponds to that of the needle protective cap (630) that may be described later.

The cap (610) comprises an internal space for the lancet (612) within which the lancet moves along a predetermined path, an internal space for the elastic element (616) within which the elastic element moves along a predetermined path and an internal space for the lancet holding member (617) within which the lancet holding member moves along a predetermined path. The above three internal spaces are connected by multi step with fine radius differences wherein the shoulder for the elastic element (613) and the end for the lancet holding member (618) may prevent the forward movement of the elastic element and the lancet holding member as the lancet moves forward.

The three internal spaces (612, 616, 617), which are connected by multi step with fine radius differences, support the lancet from both left and right sides resulting in better support of a forward movement of the lancet. Also, at the time of an impulse the movement of the elastic element (622) and the lancet holding member (623) can be stopped by the shoulder for the elastic element (613) and the end for the lancet holding member (618) resulting in less damage to the front end of the cap for a safe blood withdrawal even with a strong impulse.

Also at the rear part of the cap (610), a means for connecting (615) with the depth adjusting element (640) or the painless impulse generator using a screw type connection is formed along with outer side of the body to connect with inner side of the depth adjusting element (640).

A needle is fixed at the front end of the lancet body (620) and the front end is tapered. Also the needle protective cap (630) is defined at the front end of the lancet body (620) for an encapsulation of the needle and the protective cap (630) is detachable from the lancet body when assembling the cap to the lancet body or the cap to the painless impulse generator. The needle protective cap is automatically detached from the needle through a rotating movement of the cap when assembled with the main body of the blood withdrawal device or the painless impulse generator.

The said needle protective cap (630) which is inserted within the opening for the needle forms a multangular column thereby movable in lancing direction and rotatable together with the cap. And the diameter of the multangular column is designed to be smaller than that of the cap. Therefore the opening for the needle (611) of the cap (610) can be as small as possible thereby allowing the front end of the cap (610) to be formed thinner, which enables an accurate determination of the point for a blood withdrawal.

Although only the a square column of the needle protective cap (630) is shown in the figure, the column could be any of triangular, square, pentagonal, etc.

It is desirable that the outlet (611) for the needle, which is arranged at the front end of the cap (610), corresponds with the multangular column of the needle protective cap.

Also the lancet holding member (623) is defined at the rear part of said lancet body (620) thereby preventing an escape of a lancet from the cap due to a stop of the lancet body by a protrusion for a lancet (614). And the elastic element (622) of coil spring is inserted within the lancet body (620) thereby providing elasticity along the lancing direction.

At the rear part of the lancet holding member of said lancet body (620), a rotate stop pin (624) is defined and at the front part of the depth adjusting element (640) which is assembled to either a painless impulse generator or a main body of the blood withdrawal device, an insert hole for said rotate stop pin (644) is defined for inserting the rotate stop pin (624).

The one-piece cap and lancet (600) of the third example of the present invention comprises the needle protective cap (630) at the front end of the lancet body (620) thereby reducing the packing process after gamma sterilization. While assembling the one-piece cap and lancet (600) of the present invention with the main body of the blood withdrawal device, the one-piece cap and lancet is designed to rotate (for example, rotate clockwise) resulting in automatic detachment of the needle protective cap at the time of connecting the one-piece cap and lancet (600) with the main body of the blood withdrawal device or the depth adjusting element (640) coupled to the main body of the blood withdrawal device.

Since the needle protective cap (630) is designed to be a multangular column thereby allowing a movement only along the lancing direction through an opening for the needle (611) of the cap (610), the needle protective cap (630) rotates together with the cap (610) at the time of assembling which is done by rotating the cap. However the lancet body (620) would not rotate since the rotate stop pin defined at the rear end of the lancet body is stopped by the insert hole for the rotate stop pin (644) of the depth adjusting element (640). Therefore, if keep rotating the cap (610) then only the cap (610) and the needle protective cap (630) is subject to rotation thereby causing a twist of the cut part (B) which is a connection part for needle protective cap and lancet body resulting in automatic detachment of the needle protective cap at the moment of completion of assembling the cap.

According to the blood withdrawal device of the present invention, the needle protective cap (630) can be designed very small with the least possible volume to protect the needle since it is possible to eliminate the needle protective cap by rotating the cap (620) instead of rotating the needle protective cap by hand.

Figure 9:
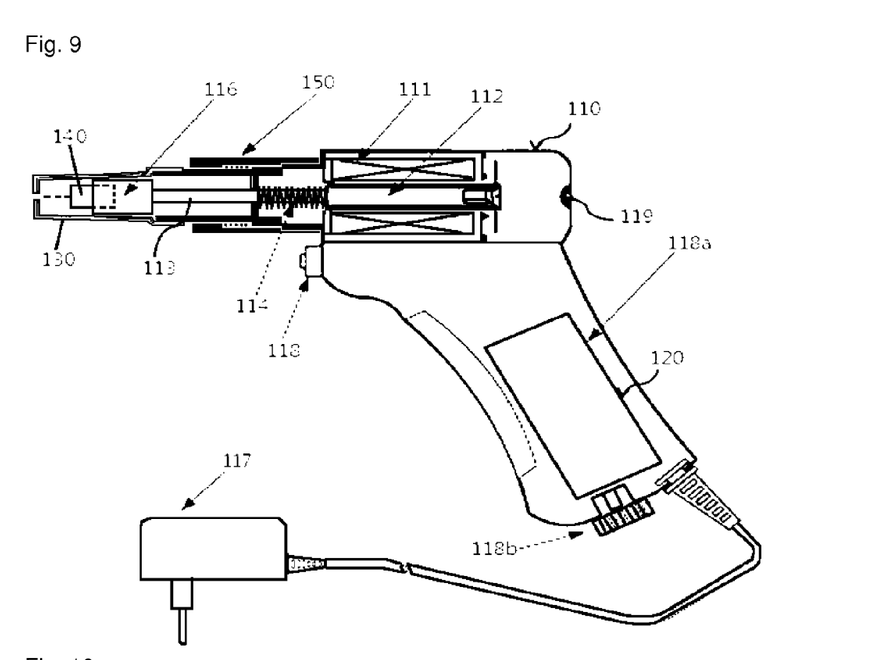
FIG. 9 is a sectional view of a strike type painless blood withdrawal device of an example of the present invention.
Figure 10:
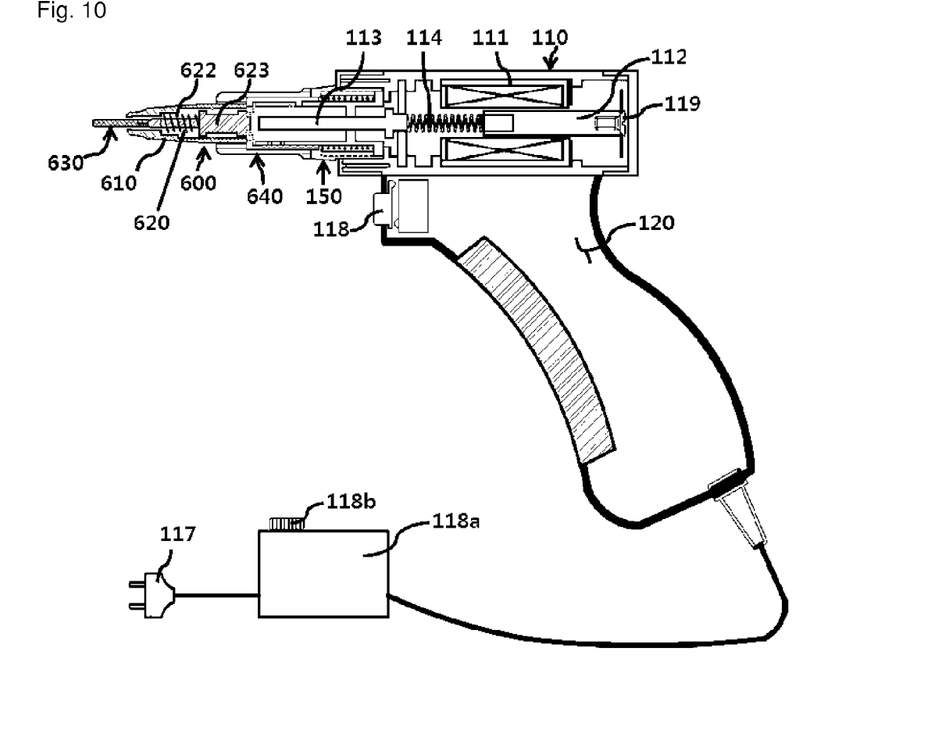
FIG. 10 and FIG. 11 are sectional views of the strike type painless blood withdrawal device of another example of the present invention.
Figure 11:
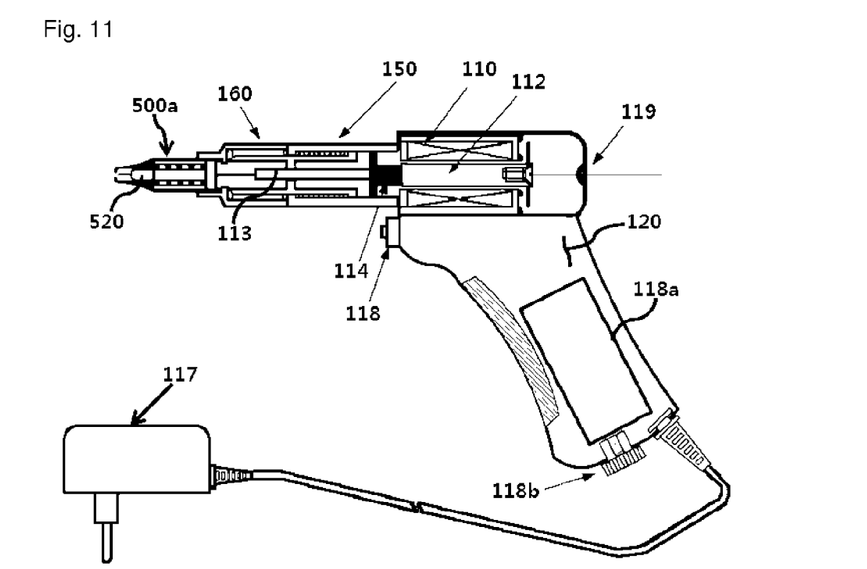

FIG. 9, FIG. 10 and FIG. 11 are sectional views of the strike type painless blood withdrawal device of the present invention. In particular, FIG. 9 presents the view of the combined state of the cap with the replaceable lancet (130) to the painless impulse generator (150), FIG. 10 presents the view of the combined state of the one-piece cap and lancet (600) of the third example to the painless impulse generator (150) through the depth adjusting element (640) and FIG. 11 presents the view of the combined state of the one-piece cap and lancet (500a) of the first example to the depth adjusting element (160). All three examples shown in FIG. 9, FIG. 10 and FIG. 11 comprise a commercial AC power connected to the painless blood withdrawal device.

As shown in FIG. 9, the strike type painless blood withdrawal device of the present invention comprises a main body (110) of the blood withdrawal device comprising an internal space with one open end, a knob (120) at the lower end of said main body of the blood withdrawal device, a solenoid (111), a plunger (112) and a movable axis (113) contained within the main body of the blood withdrawal device, a movable axis retraction unit (114) arranged on said movable axis (113), a painless impulse generator (150), a lancet holder (116) and a lancet body (140), a cap with a replaceable lancet (130), an impulse generator switch (118) arranged in the knob (120), an impulse strength adjusting unit (118a), an impulse strength adjusting lever (118b) and a power supply (117).

The solenoid (111) and the plunger (112) are contained within said main body (110) of the blood withdrawal device and the solenoid (111) is connected to the power supply (117) which supplies instantaneous pulse voltage occurred from the commercial AC power supply or the auxiliary power supply. The movable axis retraction unit (114) for retracting the plunger is defined at the front end of said plunger (112). The painless impulse generator (150) is movably defined at the open end of said main body (110) of the blood withdrawal device and the lancet holder (116) is defined at the front end of the movable axis. The lancet body (140) is fixed to said lancet holder (116) and the cap with the replaceable lancet (130) which covers the lancet is combined with the front part of said painless impulse generator (150).

The knob (120) comprises the impulse generator switch (118), the impulse strength adjusting unit (118a) and the impulse strength adjusting lever (118b) etc. Or if said power supply is designed with the auxiliary power supply, it is desirable to be arranged within the knob. The said impulse strength adjusting unit (118a) is designed to control the voltage applied to said solenoid by the value set by the impulse strength adjusting lever (118b).

The plunger (112) is inserted within the solenoid (111) and the movable axis is extended forward from the body. The plunger (112) moves forward instantaneously by the pulse voltage applied to the solenoid and then the plunger (112) is retracted backward by the movable axis retraction unit (114) that is inserted within said movable axis (113).

The main body (110) of the blood withdrawal device comprises an internal space within which the plunger (112) and the solenoid (111) are contained thereby allowing the movement along the lancing direction. Also the movable axis (113) of the plunger (112) is designed to be exposed outside by forming an opening at the front part of the main body of the blood withdrawal device.

The main body (110) of the blood withdrawal device also comprises a shock-absorbing unit (119) at the rear part of said plunger (112). It is desirable that the shock-absorbing unit (119) is made of an elastic element such as a rubber etc. in order to lessen the shock occurred between the plunger and the main body of the blood withdrawal device as the movable axis (113) moves backward by the plunger.

It is desirable that the movable axis retraction unit (114) defined at the movable axis (113) of said plunger is made of a retractable spring thereby providing a retraction power to move back to it's original position.

The lancet holder (116) is defined at the front end of the movable axis (113) which is inserted within the painless impulse generator (150), and the lancet body (140) is fixed to said lancet holder (116).

The cap with the replaceable lancet (130) is designed with the shape of a cap to cover said lancet. And the cap (130) comprises an opening for the needle at the front center of the cap where the skin contact occurs. And the lancet can be inserted within the cap or detached from the cap.

The said painless impulse generator (150) is designed with the hollow body of which diameter is connectable with the opening of the main body of the blood withdrawal device. The painless impulse generator (150) is connected to the opening of the main body of the blood withdrawal device (110) thereby movable by said plunger.

As shown in FIG. 10, the strike type painless blood withdrawal device of the present invention comprises a main body of the blood withdrawal device (110) comprising an internal space with one open end, a knob (120) at the lower end of said main body of the blood withdrawal device, a solenoid (111), a plunger (112) and a movable axis (113) contained within the main body of the blood withdrawal device, a movable axis retraction unit (114) arranged on said movable axis (113), a painless impulse generator (150), a one-piece cap and lancet (600), a needle protective cap (630), a depth adjusting element (640), an impulse generator switch (118) arranged in the knob (120), an impulse strength adjusting unit (118a), an impulse strength adjusting lever (118b) and a power supply (117).

As shown in FIG. 11, the strike type painless blood withdrawal device of the present invention comprises a main body of the blood withdrawal device (110) comprising an internal space with one open end, a knob (120) at the lower end of said main body of the blood withdrawal device, a solenoid (111), a plunger (112) and a movable axis (113) contained within the main body of the blood withdrawal device, a movable axis retraction unit (114) arranged on said movable axis (113), a painless impulse generator (150), a one-piece cap and lancet (500a), a depth adjusting element (160: see FIG. 13) connected to the painless impulse generator, an impulse generator switch (118) arranged in the knob (120), an impulse strength adjusting unit (118a), an impulse strength adjusting lever (118b) and a power supply (117).

Figure 12:
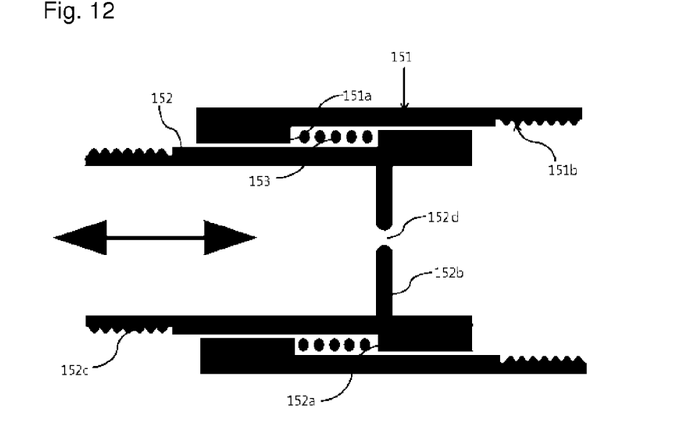
FIG. 12 is an enlarged sectional view of a painless impulse generator of FIG. 9 and FIG. 10.

FIG. 12 is an enlarged side view of the painless impulse generator of FIG. 9 and FIG. 10, and said painless impulse generator (150) comprises a fixed sleeve (151), a gearing sleeve (152), and a buffering unit (153) as shown in FIG. 12.

Both ends of the fixed sleeve (151) are open so that a shoulder for a gearing sleeve (151a) is defined at one end of the fixed sleeve and a means for connecting with the main body (151b) is defined at the other end thereby connecting the fixed sleeve (151) at the opening of the main body of the blood withdrawal device.

The gearing sleeve (152) is designed with the hollow body of which diameter is insertable within the fixed sleeve and the gearing sleeve (152) is inserted within the fixed sleeve. A means for connecting with the cap (152c) is defined at the front of the body for the connection with the cap. A partition (152b) with a hole (152d) for said movable axis is defined in the middle of the body of the gearing sleeve (152) thereby allowing the movement of the movable axis caused by the plunger as well as restricting the movement of the movable axis retraction unit (114). A shoulder for a fixed sleeve (152a) is defined at the outer side of the body of the gearing sleeve (152) so that the shoulder for a fixed sleeve (152a) is mated with a shoulder for a gearing sleeve (151a) for connection with the fixed sleeve (151).

The buffering unit (153) is made of an elastic spring etc. and is inserted between the shoulders (151a, 152a) for the fixed sleeve (151) and the gearing sleeve (152). The buffering unit (153) supported by the fixed sleeve (151) provides elasticity for the movement of the gearing sleeve.

The said painless impulse generator can be applied to an acupuncture treatment device that comprises a movable axis for a movement of a needle defined within the main body and a cap defined at the front end of a main body.

Figure 13:
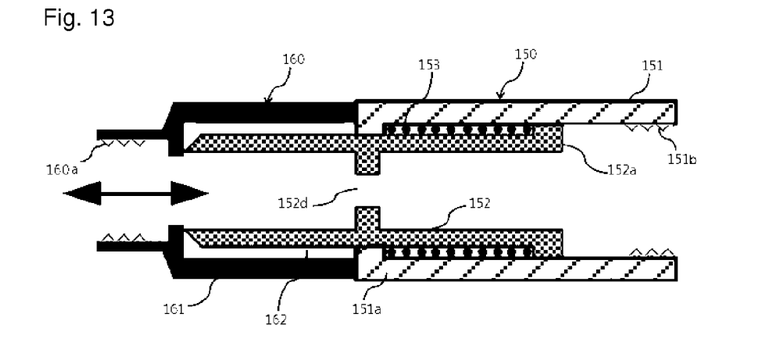
FIG. 13 is an enlarged sectional view of the painless impulse generator and the depth adjusting element of FIG. 11.

FIG. 13 is an enlarged side view of the painless impulse generator and the depth adjusting element of FIG. 11 and presents the view of the depth adjusting element (160) combined with the gearing sleeve (152) of the painless impulse generator (150).

As shown in FIG. 13, the depth adjusting element (160) comprises a depth adjusting rotating knob (161) and an inner ring (162). One end of the depth adjusting rotating knob (161) is combined with the gearing sleeve of the painless impulse generator and the other end is removably combined with the cap. Also the depth adjusting rotating knob (161) is designed to rotate trough the outer circle of said gearing sleeve.

The inner ring (162) is arranged between said depth adjusting rotating knob (161) and said gearing sleeve (152) thereby changing the distance between said cap and the main body of the blood withdrawal device depending on the rotating position of said rotating knob. Thus one end of said depth adjusting element (160) is combined with said painless impulse generator (150) thereby fixed to the main body of the blood withdrawal device and the other end is removably combined with the cap. The depth adjusting element (160) is designed to rotate trough the outer circle of said gearing sleeve and to change the distance between said cap and the main body of the blood withdrawal device depending on the degree of rotation thereby allowing an adjustment of the penetration depth of a needle as said movable axis moves forward.

The one-piece cap and lancet (300, 500, 500a) comprises the lancet body (320,520) inserted and unremovably fixed within the cap (310, 510). And the one-piece cap and lancet (300, 500, 500a) is combined with the front end of the gearing sleeve (152) of the painless impulse generator (150) or with the front end of the depth adjusting element (160) thereby moving along with said painless impulse generator or moving along both with the painless impulse generator and the depth adjusting element.

Figure 14:
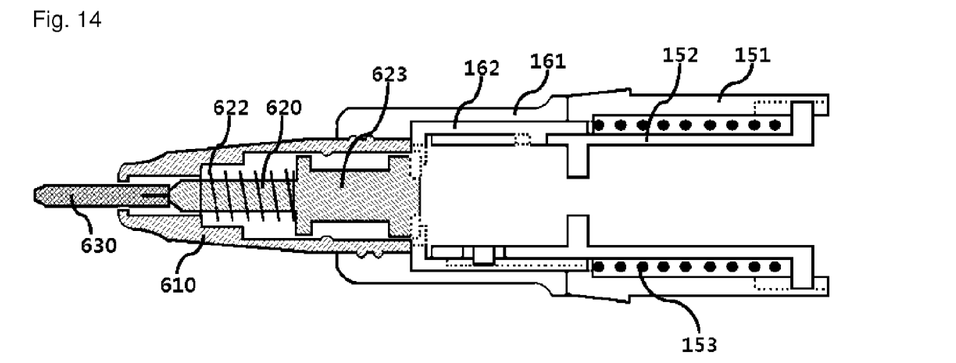
FIG. 14-FIG. 16 are enlarged sectional views of assembled and disassembled diagrams of a depth adjusting element of FIG. 13 defined between a painless impulse generator and an one-piece cap and lancet.
Figure 15:
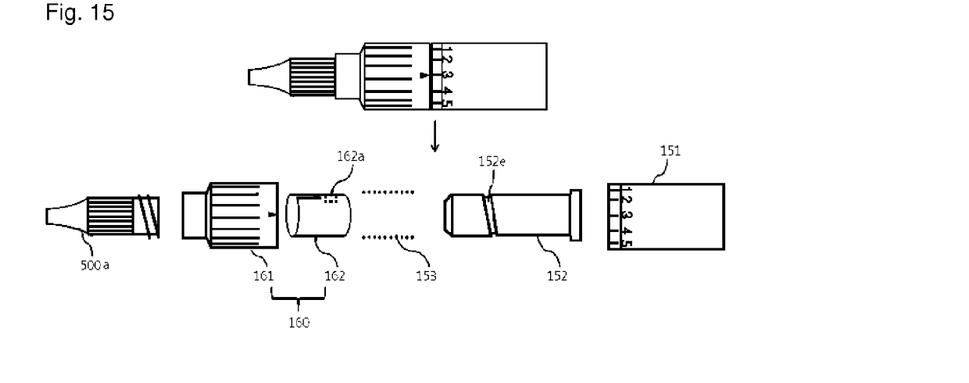
Figure 16:
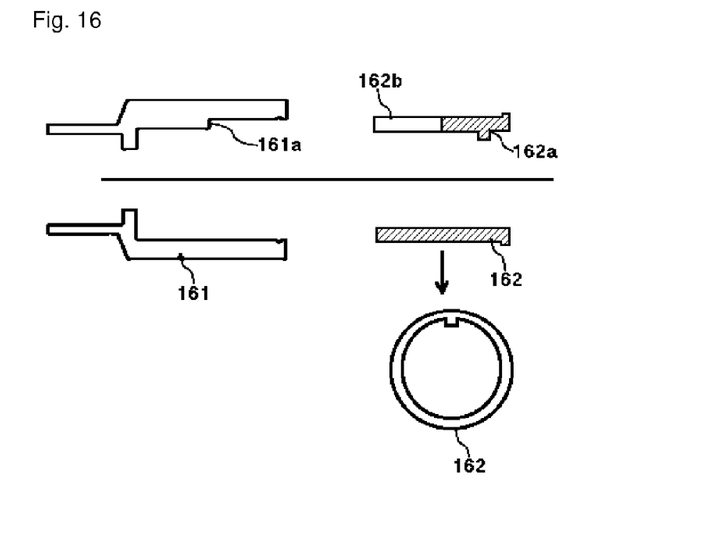
Figure 17:
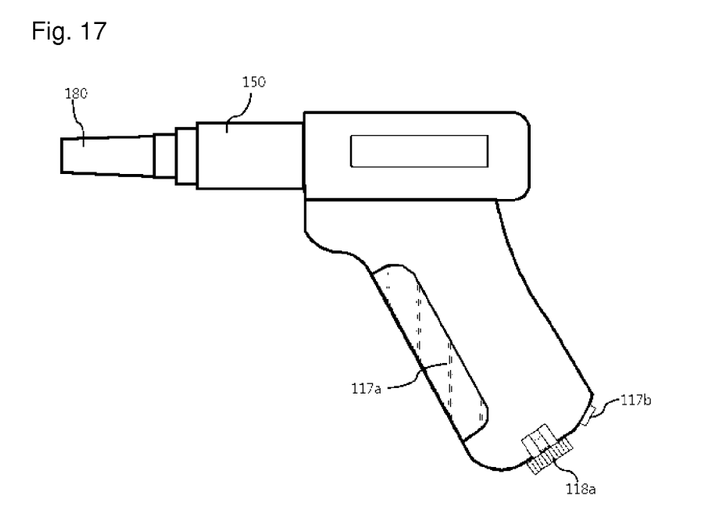
FIG. 17 is a perspective view of a touch type painless blood withdrawal device of another example of the present invention.
Figure 18:
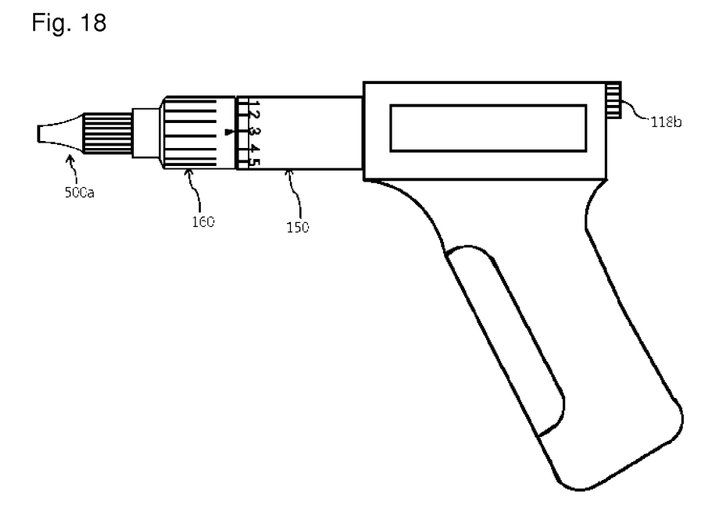
FIG. 18 and FIG. 19 are a perspective and detail views of a depth adjusting element which is combined with a touch type painless blood withdrawal device of another example of the present invention.
Figure 19:
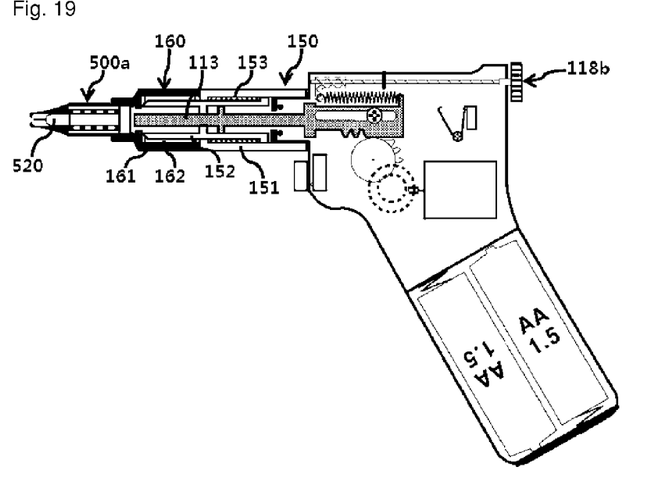

FIG. 14-FIG. 16 are an enlarged side view, an assembled view and a cutaway view which present the depth adjusting element (160) of FIG. 11 positioned between the painless impulse generator (150) and the one-piece cap and lancet (600). As shown in FIG. 14-FIG. 16, the inner ring (162) comprised of a radially slanted groove (152e) which is defined on the body of said gearing sleeve (152) and a protrusion (162a) insertable within the groove is inserted within the inner side of the depth adjusting rotating knob (161). Also a guiding rail (161a) is defined within said depth adjusting rotating knob (161) for insertion of said inner ring (162) and a guiding groove (162b) of which shape is designed to correspond to that of said guiding rail, thereby allowing a close contact connection between said inner ring (162) and the depth adjusting rotating knob (161). A control scale which is set according to the assembled state of said inner ring (162) and the gearing sleeve (152) can be indicated on the outer circle of said depth adjusting rotating knob (161). The inner ring (162) is arranged between the depth adjusting rotating knob (161) and the gearing sleeve (152) and is designed to change the distance between said cap and the main body of the blood withdrawal device depending on the degree of rotation of said rotating knob thereby allowing an adjustment of the penetration depth of a needle as said movable axis moves forward FIG. 17 is a perspective view of another example of the present invention, i.e., a touch type painless blood withdrawal device comprising a one-piece cap and lancet with a touch panel combined with a painless impulse generator. FIG. 18 and FIG. 19 are a perspective view and a partially fragmented perspective view of the touch type painless blood withdrawal device of another example of the present invention comprising a one-piece cap and lancet with a touch panel combined with the depth adjusting element. FIG. 18 and FIG. 19 also present that the cap is made of a conductive touch panel (180) and comprises a power supply circuit using an auxiliary power.

As shown in FIG. 17-FIG. 19, if the cap is made of the touch panel, a touch switch circuit, an instantaneous pulse wave circuit and an auxiliary power that are driven by the touch panel are defined within the knob. While it is not shown in the figures, the electric connection is necessary to induce a switching movement of the touch switch circuit by the touch perception signal of said touch panel. It is desirable that the auxiliary power is supplied to the instantaneous pulse wave circuit by the switching movement of the touch switch circuit.

Figure 20:
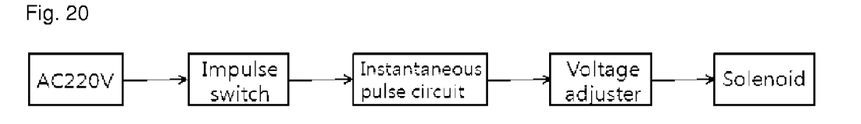
FIG. 20 is a block diagram of the painless blood withdrawal device of each examples of the present invention comprising a power supply circuit using a commercial AC power supply.
Figure 21:
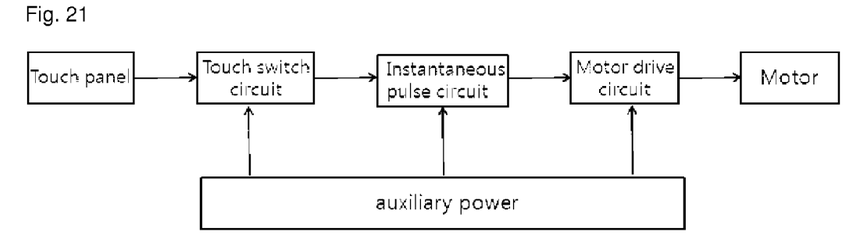
FIG. 21 is a block diagram of the touch type painless blood withdrawal device comprising a motor drive circuit using an auxiliary power.

FIG. 20 is a block diagram of the painless blood withdrawal device of each examples of the present invention comprises a power supply circuit using a commercial AC power supply. FIG. 20 also presents a power supply circuit supplying a power to a solenoid through the instantaneous pulse wave circuit and the voltage adjuster. FIG. 21 is a block diagram of a touch type painless blood withdrawal device comprising a motor drive circuit using an auxiliary power. FIG. 21 also presents a circuit driving a motor by supplying an instantaneous pulse wave circuit changed from an auxiliary power using a touch panel.

As shown in FIG. 20, the power supply circuit using a commercial power comprises a commercial AC power supply, an impulse switch for generating a pulse power control signal of a power supply, an instantaneous pulse signal from a commercial AC power supply driven by an impulse switch, for example an instantaneous pulse circuit generating ⅟₆₀ second pulse signal, a voltage adjustor controlling the output power of said instantaneous pulse wave circuit and a solenoid driving a plunger using a pulse voltage adjusted through said voltage adjustor.

As shown in FIG. 21, the motor drive circuit using the auxiliary power comprises an auxiliary power device, a touch panel and a switch circuit for generating a signal when the cap contacts with a skin, an instantaneous pulse wave circuit for generating an instantaneous pulse signal driven by a touch switch circuit and a motor drive element and a motor for generating a motor drive signal from the output of said instantaneous pulse wave circuit.

In particular, for the painless blood withdrawal device using the power supply circuit shown in FIG. 20, the impulse strength transferred in the order of a solenoid, a plunger, a painless impulse generator and a cap can be controlled by controlling the speed of the plunger. The speed of the plunger can be controlled by controlling the power supplied to the solenoid using the set value determined by the impulse strength adjusting lever (118b) and the impulse strength adjusting unit (118a) which are shown in FIG. 9 ? FIG. 11.

Figure 22:
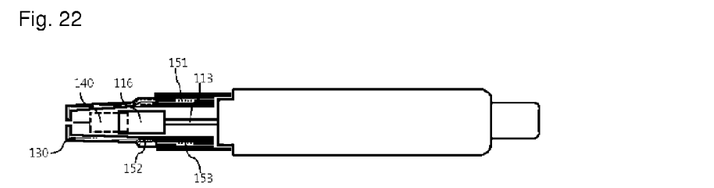
FIG. 22 is a perspective view of the pen type painless blood withdrawal device of another example of the present invention.
Figure 23:
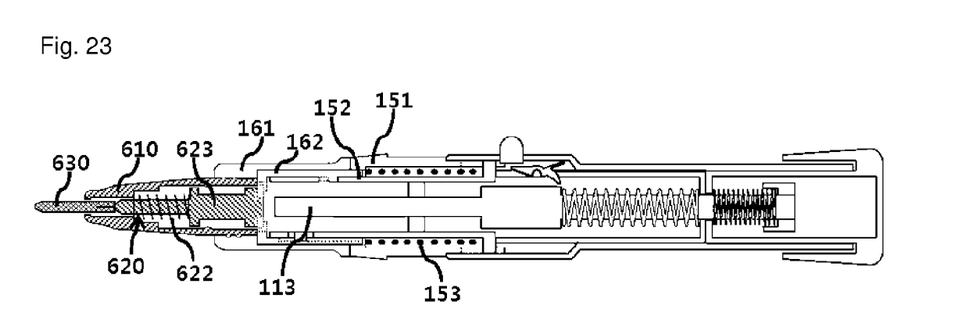
FIG. 23 is a perspective view of a pen type painless blood withdrawal device with a depth adjusting element of another example of the present invention.

FIG. 22 is a perspective view of another example of the present invention, i.e., a pen type painless blood withdrawal device comprising a cap with a replaceable lancet. FIG. 23 is a perspective view of a pen type painless blood withdrawal device of another example of the present invention comprising a depth adjusting element and a one-piece cap and lancet (600). As shown in FIG. 22 the painless impulse generator (150) can be combined at the front of the body of the pen type painless blood withdrawal device or as shown in FIG. 23 said painless impulse generator (150) can be further combined with the depth adjusting element (160), thereby striking a skin. The detailed process for striking a skin is as follows: push the button switch positioned at the back resulting in the forward movement of the movable axis (113) then the painless impulse generator or the painless impulse generator together with the depth adjusting element instantaneously moves forward at the time when the movable axis moves forward.

The movement of the painless impulse generator of each example of the present invention can be explained in two different cases. Case 1 is as follows: a cap with a replaceable lancet (130) or a cap with a replaceable lancet made of conductive material (180) is combined with a painless impulse generator (150) as shown in FIG. 9, FIG. 17 and FIG. 22. Case 2 is as follows: a one-piece cap and lancet (500a, 600) is combined with a depth adjusting element (160 or 640) within which a painless impulse generator is inserted as shown in FIG. 10, FIG. 11, FIG. 18 and FIG. 23.

In case of using the cap with the replaceable lancet (130) as shown in FIG. 9, as pressing the impulse generator switch (118), the solenoid is instantaneously charged with electric current through the power supply circuit defined within the knob (120) as shown in FIG. 20.

Thereafter the plunger (112), i.e., a drive iron core within the solenoid (111), moves forward by an instantaneous magnetic force and the movable axis retraction unit (114) that is inserted within the movable axis (130) pushes forward the partition (152b) formed at the inner side of the gearing sleeve (152) of said painless impulse generator (150). In this case the fixed sleeve (151) of the painless impulse generator (150) is fixed at the main body (110) of the blood withdrawal device without moving forward. However, since the gearing sleeve (152) that is inserted inside of said fixed sleeve (151) together with the buffering unit (153) is movably combined, the gearing sleeve (152) moves forward together with said movable axis (113) by the pushing force driven by said movable axis retraction unit (114). Therefore the cap with the replaceable lancet (130) that is combined at the front part of the gearing sleeve (152) moves forward thereby allowing the cap to strike the adjacent skin at which the needle of the lancet pricks. At the same time, the movable axis (113) moves forward together with the lancet holder (116) that is arranged at the front part of the movable axis thereby allowing the needle to prick the skin while the needle of the lancet which is combined with the lancet holder as shown in FIG. 9 strikes the skin. A painless blood withdrawal is possible by exerting an impulse on an adjacent body part at the time of a puncturing.

While in case of using the one-piece cap and lancet (600) as shown in FIG. 10, the voltage is applied to the solenoid (111) by the movement of the impulse switch (118) and then the movable axis (113) moves forward together with the plunger (112), thereafter the front end of the movable axis pushes forward the lancet holding member (623) of the one-piece cap and lancet (600), thereafter the elastic element (622) that is inserted in the lancet body (620) is compressed by the shoulder for the elastic element (613) of the cap (610) thereby moving the lancet forward along the internal space for the lancet (612) and allowing the needle to simultaneously penetrate the skin.

Also in case of using the one-piece cap and lancet (300) as shown in FIG. 6, the elastic element (322) that is defined at the lancet body (320) is bent outward by the shoulder for the elastic element (313) of the cap (310) thereby allowing the lancet to move forward along the internal space of the one-piece cap and lancet (300). And the movable axis retraction element (114) that is inserted within the movable axis (113) is compressed by the movement of said movable axis thereby allowing the partition (152b) formed at the inner side of the gearing sleeve (152) of the painless impulse generator (150) to be pushed forward, thereafter the buffering unit (153) that is inserted between the gearing sleeve (152) and the fixed sleeve (151) is compressed thereby allowing the gearing sleeve (152) to be pushed forward. Therefore the one-piece cap and lancet (600) that is combined at the front part of said painless impulse generator (150) also moves forward following the same process described referring to FIG. 10 and the cap instantaneously strikes the adjacent skin at which the needle of the lancet pricks.

According to the each example of the present inventions, the voltage applied to said solenoid is controlled by the impulse strength adjusting lever (118b) and the impulse strength adjusting element (118a) thereby controlling the impulse strength depending on part of the skin to be penetrated. Therefore it is remarkably safe and painless to withdraw blood.

The adjusting method of the skin penetrating depth by the depth adjusting element is explained as follows. First of all, a protrusion (162a) defined within the inner side of the rear end of the inner ring (162) is inserted within the radially slanted groove (152e) defined along the body of the gearing sleeve (152) thereby assembling the inner ring (162) to the gearing sleeve (152). Next, the guiding rail (161a) of the depth adjusting rotating knob (161) is inserted within guiding groove (162b) defined parallel to the lancing direction at the front end of said inner ring (162) thereby inserting said inner ring (162) within the inner side of the depth adjusting rotating knob. Therefore it is possible to combine painless impulse generator (150) movably with the depth adjusting element (160).

After finishing assembling, rotate the knob as much as it is necessary referring to the control scale which is indicated on the outer circle of said depth adjusting rotating knob (161), then according to the rotating movement of the rotating knob (161) the inner ring (162) positioned within the knob (161) rotates along the outer surface of the gearing sleeve (152)

thereby adjusting the distance between said cap and the main body of the blood withdrawal device. Therefore it is possible to adjust the penetration depth of the needle by adjusting the distance between the cap and the main body of the blood withdrawal device according to the position or rotation degree of the depth adjusting rotating knob.

Since the painless blood withdrawal device of the present invention is designed to prick the skin as the lancet strikes the cap, it can be used for a finger-pressure treatment or for a depletion of blood treatment when the lancet is removed or needle is fixed with wrong side up.

INDUSTRIAL APPLICABILITY

The one-piece cap and lancet of the present invention has a simple construction of a cap and lancet body in one-piece and provides a simple and easy blood withdrawal by introducing an elastic element within the cap thereby providing elasticity to the movement of a needle. Since the device is disposable, the danger of a secondary infection can be remarkably reduced and the burden of replacing lancets is eliminated. Therefore a remarkable growth in the market is expected in the future.

The painless blood withdrawal device of the present invention strikes the adjacent skin at the time of pricking the skin thereby allowing pricking without sensing a pain, painless blood withdrawal is possible. Therefore a great deal of demand is expected from patients, hospitals and doctor's office etc.

The invention claimed is:

1. A one-piece cap and lancet comprising:
   (i) a hollow body cap including an internal space, wherein a lancet is movable within the internal space, wherein the internal space forming a multi-step structure defines a shoulder for an elastic element to stop the forward movement of the lancet, wherein an opening for a needle is defined at the front end of the hollow body cap, and wherein a projection for the lancet is defined at the rear end of an inner circle of the hollow body cap;
   (ii) a lancet body movably contained within the internal space of the hollow body cap, wherein the needle is fixed at the front end of the lancet body, wherein a lancet holding member is formed at the rear end of the lancet body for preventing an escape of the lancet, and wherein the needle moves along a predetermined path through an opening for allowing the needle to advance therethrough;
   (iii) an elastic element providing elasticity for the movement of the lancet together with the lancet body contained in the internal space of the hollow body cap, and
   (iv) a painless impulse generator detachably connected to the hollow body cap, with the painless impulse generator comprising a power supply supplying a pulse power through an instantaneous pulse wave circuit, and an impulse generator switch controlling the pulse power of said power supply,
   wherein the elastic element providing elasticity for the movement of the lancet is defined between the shoulder for the elastic element and the lancet holding member of the lancet body,
   wherein the elastic element is detachable from the lancet forming a shape of a jar whose middle is convex to bend toward the lancet body, and wherein one end of the elastic element is connected to the shoulder for the elastic element and the other end is connected to the lancet holding member, and
   wherein the elastic element is comprised of two or more rings overlapped to strengthen elasticity.

2. The one-piece cap and lancet of claim 1, further comprising a needle protective cap defined at the front end of the lancet body for an encapsulation of the needle.

3. The one-piece cap and lancet of claim 2, wherein the needle protective cap is automatically detached from the needle through a rotating movement of the needle protective cap when assembled with the painless impulse generator.

4. The one-piece cap and lancet of claim 2, wherein the needle protective cap being inserted within the opening for the needle is movable in a lancing direction, said needle protective cap being multi-angular thereby rotating together with said hollow body cap, wherein the shape of the opening for the needle is multi-angular corresponding to that of said hollow body cap.

5. The one-piece cap and lancet of claim 4, wherein a diameter of said needle protective cap is designed that the diameter is smaller than that of said hollow body cap.

6. The one-piece cap and lancet of claim 2, further comprising a rotate stop pin and a depth adjusting element, wherein said depth adjusting element is assembled to the painless impulse generator or a main body of a blood withdrawal device, wherein said rotate stop pin is defined at the rear end of the lancet holding member thereby preventing a rotation of the lancet body, and wherein an insert hole for said rotate stop pin is defined at the front end of said depth adjusting element thereby inserting the rotate stop pin.

* * * * *